United States Patent
Barnes et al.

(10) Patent No.: US 9,993,259 B2
(45) Date of Patent: Jun. 12, 2018

(54) SYSTEMS, DEVICES, AND METHODS FOR ACCESSING BODY TISSUE

(71) Applicant: Mayo Foundation for Medical Education and Research, Rochester, MN (US)

(72) Inventors: Darryl E. Barnes, Byron, MN (US); Jay Smith, Byron, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days. days.

(21) Appl. No.: 15/402,127

(22) Filed: Jan. 9, 2017

(65) Prior Publication Data

US 2017/0189050 A1    Jul. 6, 2017

Related U.S. Application Data

(63) Continuation of application No. 12/663,640, filed as application No. PCT/US2009/034659 on Feb. 20, 2009, now abandoned.

(60) Provisional application No. 61/030,009, filed on Feb. 20, 2008.

(51) Int. Cl.
| | |
|---|---|
| *A61B 17/32* | (2006.01) |
| *A61B 17/16* | (2006.01) |
| *A61B 34/20* | (2016.01) |
| *A61B 8/14* | (2006.01) |
| *A61B 17/3205* | (2006.01) |
| *A61B 17/3211* | (2006.01) |
| *A61B 18/20* | (2006.01) |
| *A61B 17/00* | (2006.01) |
| *A61B 17/22* | (2006.01) |

(Continued)

(52) U.S. Cl.
CPC ........ *A61B 17/320036* (2013.01); *A61B 8/14* (2013.01); *A61B 17/1604* (2013.01); *A61B 17/1615* (2013.01); *A61B 17/1624* (2013.01); *A61B 17/3205* (2013.01); *A61B 17/3211* (2013.01); *A61B 34/20* (2016.02); *A61B 17/1637* (2013.01); *A61B 18/20* (2013.01); *A61B 2017/00424* (2013.01); *A61B 2017/00734* (2013.01); *A61B 2017/22025* (2013.01); *A61B 2017/320052* (2013.01); *A61B 2017/3413* (2013.01); *A61B 2090/378* (2016.02); *A61B 2217/005* (2013.01); *A61B 2217/007* (2013.01)

(58) Field of Classification Search
None
See application file for complete search history.

(56) References Cited

U.S. PATENT DOCUMENTS

| | | | | |
|---|---|---|---|---|
| 5,747,953 | A | * | 5/1998 | Philipp .............. A61B 17/1626 318/114 |
| 5,814,016 | A | * | 9/1998 | Valley .............. A61B 17/00234 604/96.01 |

(Continued)

*Primary Examiner* — Katherine Fernandez
(74) *Attorney, Agent, or Firm* — K&L Gates LLP; Louis C. Cullman; Robert W. Winn

(57) ABSTRACT

Systems, devices and methods to access and/or treat targeted body tissue (e.g., tendon tissue, ligament tissue, muscle tissue, bony tissue, and the like) under the guidance of ultrasound imaging equipment are described. Such systems can permit the intra-operative identification of the targeted tissue and the ability to deliver the appropriate instrumentation to that tissue.

18 Claims, 7 Drawing Sheets

(51) Int. Cl.
*A61B 17/34* (2006.01)
*A61B 90/00* (2016.01)

(56) References Cited

U.S. PATENT DOCUMENTS

| | | | | |
|---|---|---|---|---|
| 6,102,046 | A * | 8/2000 | Weinstein | A61M 25/0133 128/898 |
| 6,980,419 | B2 * | 12/2005 | Smith | A61B 90/36 361/679.21 |
| 8,303,505 | B2 * | 11/2012 | Webler | G06F 19/3437 600/437 |
| 2004/0133168 | A1 * | 7/2004 | Salcudean | A61B 10/04 604/164.13 |
| 2007/0250041 | A1 * | 10/2007 | Werp | A61M 25/0122 604/529 |
| 2007/0276352 | A1 * | 11/2007 | Crocker | A61B 10/025 604/500 |

* cited by examiner

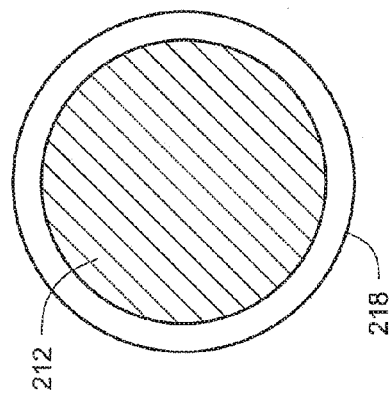
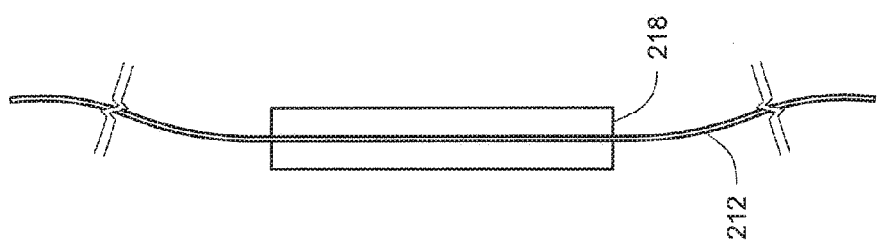

SYSTEMS, DEVICES, AND METHODS FOR ACCESSING BODY TISSUE

CROSS REFERENCE TO RELATED APPLICATIONS

The present application is a continuation of U.S. patent application Ser. No. 12/663,640 filed Jan. 9, 2017, which claims the benefit under 35 U.S.C. § 119(e) of U.S. Provisional Applications No. 61/030,009, titled ACCESSING AND TREATING BODY TISSUE, filed on Feb. 20, 2008. Both applications are incorporated herein by reference in their entirety.

Systems, devices and methods for accessing body tissue using percutaneous percutaneously techniques are described herein.

Repetitive motion or use of body tissues can cause injuries or painful conditions to arise. For example, tennis elbow, or lateral eplicondylalgia is a clinical syndrome in which patients experience pain at the lateral elbow. Such pain in the lateral elbow may be worsened during heavy gripping, repetitive use, palpation, and resisted wrist or middle finger extension. Despite adequate treatment, many patients develop chronic symptoms and eventually become candidates for surgical treatment.

A number of surgical procedures have been described to treat conditions such as, e.g., chronic lateral epicondylagia, etc. Particular open techniques typically require open surgical dissection down to the pathological tissue and therefore necessitate repair of the surgically compromised normal tissue. Some anthroscopic techniques can be slightly less invasive, but these anthroscopic elbow techniques have been associated with neurological complications and may require the use of a high-cost operating suite and associated personnel. Various percutaneous techniques have been described which release, ablate or resect the pathological tissue. These percutaneous techniques generally require a noticeable skin incision, some surgical dissection, and the use of a high-cost operating suite and supportive equipment and personnel.

SUMMARY

Systems, devices and methods for accessing and/or treating targeted body tissue (e.g., tendon tissue, ligament tissue, muscle tissue, bony tissue, and the like) under the guidance of ultrasound imaging equipment are described herein. Such systems can permit the intra-operative identification of the targeted tissue and the ability to deliver the appropriate instrumentation to that tissue. For example, a high-frequency ultrasound transducer and associated ultrasound imaging equipment can provide visual detail of the tendinopathic changes of lateral epicondylalgia, so the pathologic tissues can be identified in their entirety at the time of a procedure without the need to cut the skin. Thereafter, the pathologic tissue or other targeted tissue can be accessed and treated using a cannula that is connectable to a handheld driver device. Other tissues in the elbow joint and in other parts of the body are also contemplated for treatment using the system described herein.

The apparatus and techniques described herein can provide disruption of the targeted tissue and may also provide debridement of pathological tissue, decortication of the adjacent bone, or both. For example, the systems and techniques described herein may provide ultrasound-guided percutaneous tenotomy for chronic lateral epicondylalgia. The use of ultrasound equipment and echogenic instrumentation may provide for precise localization and treatment of the pathological tissue under real-time guidance while minimizing trauma to non-affected tissues. In addition, the apparatus described herein may serve to deliver therapeutic agents to the site after the tissue is treated. The techniques described herein can, in many instances, be performed by a skilled radiologist, orthopedist, family practitioner, or physiatrist as part of an office-based procedure under local anesthesia, with equipment of nominal cost, and minimal supportive personnel. These potential advantages may not only improve patient satisfaction, but may also result in cost-savings by avoiding the opportunity and direct costs of operating room time.

In one aspect, a system for treating body tissue under guidance of ultrasound instrumentation is provided, the system including a cannula to percutaneously access targeted tissue, the cannula comprising a distal tip portion that comprises with, optionally, a lateral width of 12 gauge or less, the distal tip portion comprising an echogenic material so as to be viewable by ultrasound imaging equipment; an elongate instrument that is insertable into a proximal opening of the cannula and through a distal opening of the cannula, the elongate instrument having a working tip to act upon the targeted tissue, the working tip comprising an echogenic material so as to be viewable by ultrasound imaging equipment; and a handheld driver unit having a powered actuator to drive the working tip of the elongate instrument to act upon the targeted tissue, wherein the handheld driver unit is releasably securable to the cannula such that at least a portion of the elongate instrument resides in the cannula.

In another aspect, a method of ultrasound-guided percutaneous tenotomy is provided, the method unlading disposing an ultrasound transducer device over a portion of skin proximate to targeted tendon tissue; monitoring under the guidance of ultrasound imaging equipment the insertion of an echogenic distal tip portion of a cannula toward the targeted tendon tissue; releasably securing a handheld driver unit to a proximal portion of the cannula extending outside the skin such that an elongate instrument coupled to the handheld driver unit resides at least partially in the cannula; and viewing the ultrasound imaging equipment as a working tip of the elongate instrument acts upon the targeted tendon tissue.

In another aspect, a system for treating body tissue under guidance of ultrasound instrumentation is provided, the system including a cannula to percutaneously access targeted tissue, the cannula having a distal tip portion that includes echogenic material so as to be viewable by ultrasound imaging equipment; an elongate working instrument that is insertable into a proximal opening of the cannula and through a distal opening of the cannula, the elongate working instrument having a working shaft that includes a working tip to act upon the targeted tissue, the working tip comprising echogenic material so as to be viewable by ultrasound imaging equipment; and a handheld driver unit having a powered actuator to drive the working tip of the elongate working instrument to act upon the targeted tissues wherein the handheld driver unit is releasably securable to the cannula such that at least a portion of the elongate working instrument resides in the cannula.

In various embodiments, the systems may include one or more of the following features: the cannula may include an adjustable length, such that the distance between the distal tip portion of the cannula and the handheld driver unit is adjustable; the cannula may have an adjustable cross-sectional area; the cannula may have a lateral width of about 12 gauge or less; a trocar may be located within the cannula, wherein the trocar has a pointed tip protruding from the distal tip portion of the cannula; the working tip of the working instrument may be selected from the group consisting of a drill tip, a chisel tip, a burr device, and a micro-augur device; the working shaft may have an adjustable length, wherein the distance between the working tip and the proximal opening of the cannula is adjustable; the working shaft may be smaller than an inner diameter of the cannula such that an outer lumen is defined between the working shaft and the inner diameter of the cannula; the working shaft may be a hollow working shaft such that fluid can pass between a proximal port and a distal opening of the working shaft; the working shaft may be smaller than an inner diameter of the cannula such that as outer lumen is defined between the working shaft and the inner diameter of the cannula, and the working shaft and may be a hollow working shaft such that fluid can pass between a proximal port and a distal opening of the working shaft; the working tip may include a micro-auger; etc.

In another aspect, a method of ultrasound-guided percutaneous tenotomy is provided, the method including disposing an ultrasound transducer device over a portion of skin proximate to targeted tendon tissue; monitoring under the guidance of ultrasound imaging equipment the insertion of an echogenic distal tip portion of a cannula toward the targeted tendon tissue; releasably securing a handheld driver unit to a proximal portion of the cannula extending outside the skin such that an elongate working instrument coupled to the handheld driver unit resides at least partially in the cannula; and viewing the ultrasound imaging equipment as a working tip at a distal end of a working shall of the elongate working instrument acts upon the targeted tendon tissue.

In various embodiments, the methods may include one or more of the following features: the cannula may have an adjustable length, and the method may include adjusting the distance between the distal tip portion of the cannula and the handheld driver unit; the working shaft may include an adjustable length, and the method may include adjusting the distance between the working tip and the proximal opening of the cannula; the working shaft may be smaller than an inner diameter of the cannula such that an outer lumen is defined between the working shaft and the inner diameter of the cannula, and the method may include moving fluid through the outer lumen; the working shaft may be a hollow working shaft such that fluid can pass between a proximal port and a distal opening of the working shaft, and the method may include moving fluid through the hollow working shaft; the working shaft may be smaller than an inner diameter of the cannula such that an outer lumen is defined between the working shaft and the inner diameter of the cannula and the working shaft may be a hollow working shaft such that fluid can pass between a proximal port and a distal opening of the working shaft, and the method may include moving fluid through the outer lumen and the hollow working shaft; etc.

The details of one or more embodiments are set forth in the accompanying drawings the description below. Other features and potential advantages will be apparent from the description and drawings, and from the claims.

BRIEF DESCRIPTION OF DRAWINGS

FIGS. 7A and 7B are views of a portion of the system of FIG. 5.

Like reference symbols in the various drawings indicate like elements.

DETAILED DESCRIPTION OF ILLUSTRATIVE EMBODIMENTS

Figure 1:
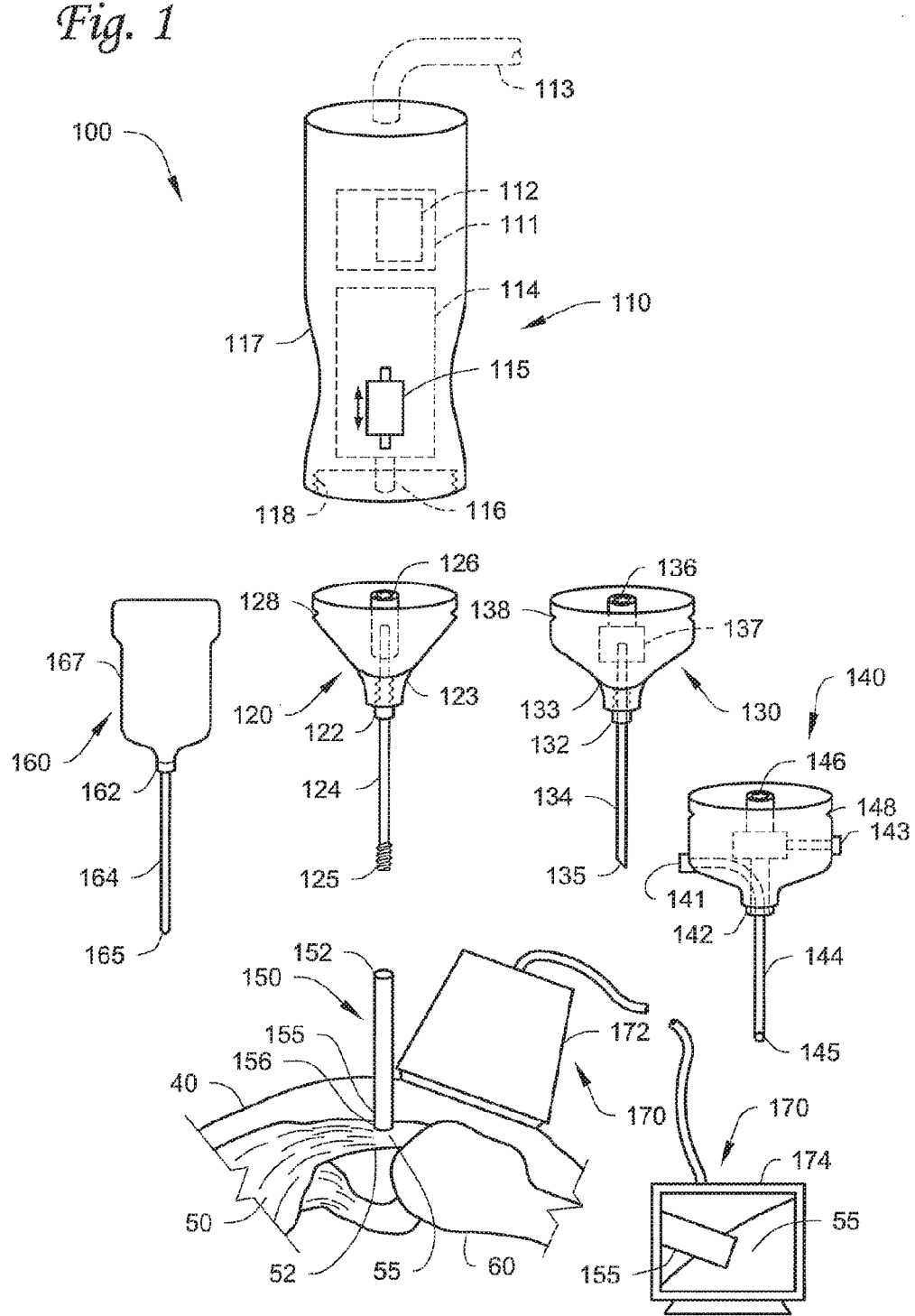
FIG. 1 is a perspective view of a system for accessing and treating tissue in accordance with some embodiments.

In the following detailed description of illustrative embodiments, reference is made to the accompanying figures of the drawing which form a part hereof, and in which are shown, by way of illustration, specific embodiments of this disclosure. It is to be understood that other embodiments may be utilized and structural changes may be made without departing from the scope of the present disclosure.

Referring to FIG. 1, some embodiments of a medical system 100 can be used to percutaneously access and act upon targeted tissue, while reducing the likelihood of trauma to healthy soft tissue. In certain circumstances, the system 100 may permit a patient to be treated in an office-based procedure under local anesthesia, thereby resulting in cost-savings to the patient and health care system by avoiding the costs of operating room time. In the embodiment depicted in FIG. 1, the targeted tissue 55 is accessed via a small-sized cannula 150 under the guidance of ultrasound imaging equipment 170. Accordingly, the user may be provided with the ability for intra-operative identification of the targeted tissue 55 and the ability to deliver the one or more working instruments to that tissue 55. For example, some embodiments of the system 100 can be employed to perform: fenestration or release of scar tissue in tendon, ligament, muscle, and fascia; disruption and removal of soft tissue calcification; debridement of soft tissue, cartilage, or bone; soft tissue coagulation; burring and/or fenestration of bony surfaces; disruption and aspiration of cysts and fluid filled structures; delivery of therapeutic agents; or a combination thereof.

In the embodiment depicted in FIG. 1, the cannula 150 provides access through a portion of skin 40 and to a targeted area 55 of a tendon 52 that connects a muscle 50 to a bone 60. Such targeted tissue 55 may include tendinopathic tissue in the lateral epicondylalgia or in other parts of the body such as the shoulder joint (e.g., rotator cuff), the knee joint, or the like.

The system 100 may include a hand-operated driver device 110 that can actuate one or more working instruments 120, 130, 140 to act upon the targeted tissue 55. In this embodiment, driver device 110 is a multi-functional, held-motorized device utilized for percutaneous treatment of soft tissue and bony lesions. The driver device 110 and the working instrument 120 coupled thereto may be configured for use with ultrasound guidance.

The driver device 110 can be a battery-powered, rechargeable apparatus that is configured to fit within the grasp of a user's hand. For example, as shown in FIG. 1, the driver device 110 may include a controller unit 111 that is coupled to a battery power source 112. The battery source 112 can be a rechargeable unit that is disconnectable to receive recharge power via a desktop charger unit. Optionally, the battery source 112 can be recharged by a power cord 113 that is connected to a power outlet. Alternatively, the driver device 110 may operate directly from the power provided by the power cord 113 (e.g., without the use of a rechargeable battery unit 112).

An electrically powered actuator 114 may be disposed within the driver device 110 and may be connected to the battery power source 112 (e.g., either directly or via the controller unit 111). In this embodiment, the powered actuator 114 is a motor that includes a referable output shaft 116. The user can adjust a trigger member 115 so as to activate the motor to rotate the shaft 116 in a fast direction or an opposite, second direction. In other embodiments, the electrically powered actuator 114 may comprise a linear actuator wherein the output shaft 116 reciprocates in an axial direction (forward/rearward). Alternatively, the electrically powered actuator 114 may comprise device that outputs rotational motion or reciprocating axial motion in response to the input from the user (e.g., press the trigger member 115 inward toward the housing 117 to cause reciprocating axial movements and sliding the trigger member longitudinally along the housing 117 to cause rotational movement). In addition or in the alternative to the finger-operated trigger member 115, user may adjust a foot-operated switch that is either electrically connected to the driver device 110 or wirelessly coupled to the driver device 110 (e.g., via bluetooth communication technology). Such embodiments may permit one or more output functions (e.g., speed, rotational direction, or the like) to be regulated by a mechanism other than the controls located on the driver device 110 itself.

Still referring to FIG. 1, the driver device 110 may be economically configured to fit within the user's hand. In some embodiments, the driver device 110 may include a housing 117 that has contoured surfaces to facilitate grasping by the user. The housing 117 may comprise a lightweight material, such as a polymer (e.g., Acrylonitrile Butadiene Styrene or the like) so that the driver device is readily maneuvered by the user (e.g., may have an overall weight of about 16 oz or less).

The trigger member 115 may be ergonomically positioned to align a user's thumb or other fingers when the driver device 110 is held in the user's hand. Other buttons or switches may be provided on the driver device 110. For example, the user may turn a dial or press a button to adjust the amplitude of reciprocation movement of the output shaft 116 between about 1 mm and about 25 mm. In another example, the user may turn a dial or press a button to adjust the rotation speed of the output shaft 116.

As shown in FIG. 1, the driver device 110 may be connected to one or more working instruments 120, 130, 140 that can pass through an access cannula 150 to act upon the targeted tissue 55. In this embodiment, the driver device 110 can releasably couple with any one of a number of working instruments 120, 130, and 140. As described in more detail below, the access cannula 150 can releasably couple with the driver device 110 so that the working instrument 120, 130, or 140 is maneuvered proximate the targeted tissue in conjunction with the access cannula 150. It should be understood that, in some embodiments, the driver device 110 may be fixedly connected with a working instrument that extends from the device housing 117 for insertion into the access cannula 150.

In this embodiment the driver device 110 can be connected with a working instrument in the form of drill tip instrument 120 so that the output shaft 116 aligns with and mates to a complementary coupler 126. The drill tip instrument 120 may include a connector 128 that mates to a connector 118 of the driver device 118 as to releasably secure the components to one another. The connectors 118 and 128 may comprise a complementary thread pattern, snap-fit groove and channel connectors, or the like.

When the drill tip instrument 120 is connected to the driver device 110, the output shaft 116 may be activated to cause rotation of working shall 124. The working shaft 124 includes a working tip portion 125 that may include, for example, a drill bit pattern that acts upon the targeted tissue when rotated. In some embodiments, the working shaft 124 may be adjustable relative to the driver device 110. For example, the drill tip instrument 120 may include a dial 123 having an internal thread pattern that can be shifted to axially adjust the longitudinal extension of the working shaft 124. In this embodiment, the dial 123 can be turned so that the internal threads act upon external threads of the proximal portion of the working shaft 124, thereby causing the proximal portion of the working shaft 124 to adjust axially rearward (further into the coupler 126) or axially forward (further out of the coupler 126).

In some instances, the working tip 123 of the drill tip instrument 120 may be used to drill bony or cartilaginous lesions, or scarred and fibrotic tissue. The working tip 125 may also be used to drill cortical holes for the purposes of stem cell migration, from bone marrow. Furthermore, in some embodiments, the working shall 124 may have a hollow core to core out cylinders of soft tissue or other debris.

Still referring to FIG. 1, the cannula 150 may provide a conduit for the working tip 125 of the instrument 120 to pass from the outside the patient's body to the targeted tissue area 35. Maintaining this conduit allows the operator to exchange working tips while leaving the cannula 150 in place, thereby increasing the functionality of the system 100. The driver device 110 and the working instrument 120 can be releasably coupled to the access cannula 150. For example, the access cannula 150 can include a connecter 152 along its proximal portion so as to releasably secure to the connector dial 122 of the working instrument 120 (which is secured to the driver device 110 as previously described).

In some embodiments, the length of the cannula 150 extending from the driver device 110 can be adjusted so as to regulate the amount of working tip exposed. For example, a proximal portion of the cannula 150 may include a connector 152 (e.g., an external thread pattern or the like) that abates with a connector 122 of the working instrument 120. At this interface, the cannula 150 or the dial 122 can be turned to adjust cannula 150 extension length relative to the working tip 125. For instance, by rotating the cannula 150 clockwise or counterclockwise, the extension length relative to the working tip 125 may be increased or decreased, respectively. Such extension length adjustments allow operator control of working fields within the target area.

In some embodiments, the access cannula 150 may be configured to provide cross-sectional area expandability. For example, the access cannula may be directed toward the targeted tissue while in a non-dilated condition, and then the cannula 150 may be adjusted or dilated so as to expand its cross-sectional area. Thus, in such embodiments, a cannula 150 of a smaller gauge may be expanded in size to facilitate removal of larger tissue debris.

In the embodiment depicted in FIG. 1, the cannula 150 may include a thin-walled hollow tube comprising stainless steel or another echogenic material. In some embodiments, the access cannula 150 may be a miniature cannula having a relatively small lateral width so as to reduce the trauma to health tissue proximate to the targeted tissue 55. For example, the access cannula 150 may have a size of about 12 gauge or less, about 12 gauge to about 25 gauge, about 14 gauge to about 22 gauge. Alternatively, the cannula 150 may have a lateral width of about 2.5 mm or less, about 2.2 mm to about 0.4 mm, about 2.1 mm to about 0.5 mm. In some embodiments, the length of the access cannula 150 may be about 3.0 inches to about 0.23 inches, about 2.7 inches to about 0.5 inches, and about 2.5 inches to about 1.0 inch. The stainless steel of other echogenic material of the access cannula 150 permits at least the distal portion 155 of the cannula 150 to be visualized with ultrasound imaging equipment 170. In some circumstances, the cannula may be coated or etched for increased echogenicity. Alternatively, if the cannula 150 is formed from a disposable plastic material, the cannula itself can be engineered, coated, or etched to increase the echogenicity of the plastic body.

The access cannula 150 may include a tapered distal end 156 having a distal opening through, which the working tip 125 passes. The tapered distal end 156 may provide for atraumatic skin and soft tissue penetration. As shown in FIG. 1, the cannula 150 may receive a trocar device 160 to facilitate advancement of the cannula 150 through the skin and soft tissue. The trocar device 160 may include a handle portion 167 and a solid shaft 164 that is receivable in the cannula 150. The connector 152 of the cannula 150 can be releasably secured to a connector 162 of the trocar device 160 so that the shaft 164 and the distal portion 155 of the cannula 150 can be advanced through the tissue together.

In some circumstances, the trocar device 160 may include a pointed tip 165 that facilitates the penetration through the tissue. As such, the cannula tip 156 may be blunt and for introduction through the skin and soft tissue, and the trocar tip 165 facilitates the penetration. After reaching the target tissue 55, the trocar device 160 can be released and removed form the cannula 130 while the cannula remains in place to provide the access port for the working instrument (e.g., 120/130/140). In some embodiments, both the trocar device 160 and the cannula 150 may be discarded after one use. Alternative, the trocar device 160 and the cannula 150 may be reused after sterilization.

Still referring to FIG. 1, when the trocar device 160 is removed from the cannula 150, the working instrument 120 may be secured to the driver device 110 and the a advanced into the cannula 150. The proximal connector 152 of the cannula can releasably secure to the connector 122 so that the cannula is releasably coupled to the driver device 110 while the working shaft 122 operates within the cannula 150.

As described in more detail herein, the advancement of the cannula 150 and the subsequent insertion of the working tip (e.g., 123/133/143) may be performed under guidance of ultrasound imaging equipment 170. Such systems can permit the intra-operative identification of the targeted tissue 55 and the ability to deliver the appropriate instrumentation to that tissue 55. For example, a high-frequency ultrasound transducer 172 and associated ultrasound imaging devices 174 can provide visual detail of the tendinopathic changes of a particular tendon 52, thereby enabling the pathologic tissues to be identified in their entirety at the time of a procedure without the need to cut the skin 40. Thereafter, the pathologic tissue or other targeted tissue 55 can be accessed and treated using the cannula 150 and working tip introduced therethrough.

As shown in FIG. 1, at least the tip portion 155 of the cannula 150 comprises an echogenic material so that the tip portion 153 is viewable on the ultrasound imaging device 174. Similarly, the working tip 125 of the working instrument 120 is also viewable on the device 174 when the working tip 123 is introduced to act upon the targeted tissue 55.

Still referring to FIG. 1, as previously described, a number of different working instruments can be introduced through the cannula 150. For example, a working instrument 130 may include a working shaft 134 that provides a chisel or awl-like tip 135. The working shaft may be solid and may comprise stainless steel or another echogenic material. In some embodiments, the working instrument 130 or at least the shaft 134 may be disposable. As previously described, the working shall 134 is sized to fit through the cannula 150. For example, the working shaft 34 may have a size of about 16 gauge to about 27 gauge and may have an extension length of about 3 inches to about 0.25 inches. The pointed tip region 135 may be supplied in a number of stiffness configurations depending upon tissue to be treated.

The working instrument 130 may have a coupler 136 that couples to the shaft 116 of the driver device 110, and the connector 138 releasably secures the working instrument 130 to the mating connector 118 of the driver device 110. The output shaft 116 may provide a reciprocating forward-backward mode for soft tissue fenestration, disruption of osteocartilaginous lesions, and bony fenestration. Alternatively, the working instrument may include a mechanism 137 that translates the rotational motion of the output shaft 116 to the axial reciprocating movement for the working shaft 134. As previously described, the working instrument 130 may include a connector 132 to releasably secure the proximal portion 152 of the cannula. As such, the cannula 150 can be releasably coupled to the driver device 110 while dm working shall 134 reciprocates therein. Furthermore, when motor 114 of the driver device 110 is powered off, the working tip 135 may be used as a probe. In some embodiments, the working tip 135 may include a serrated region.

Figure 2:
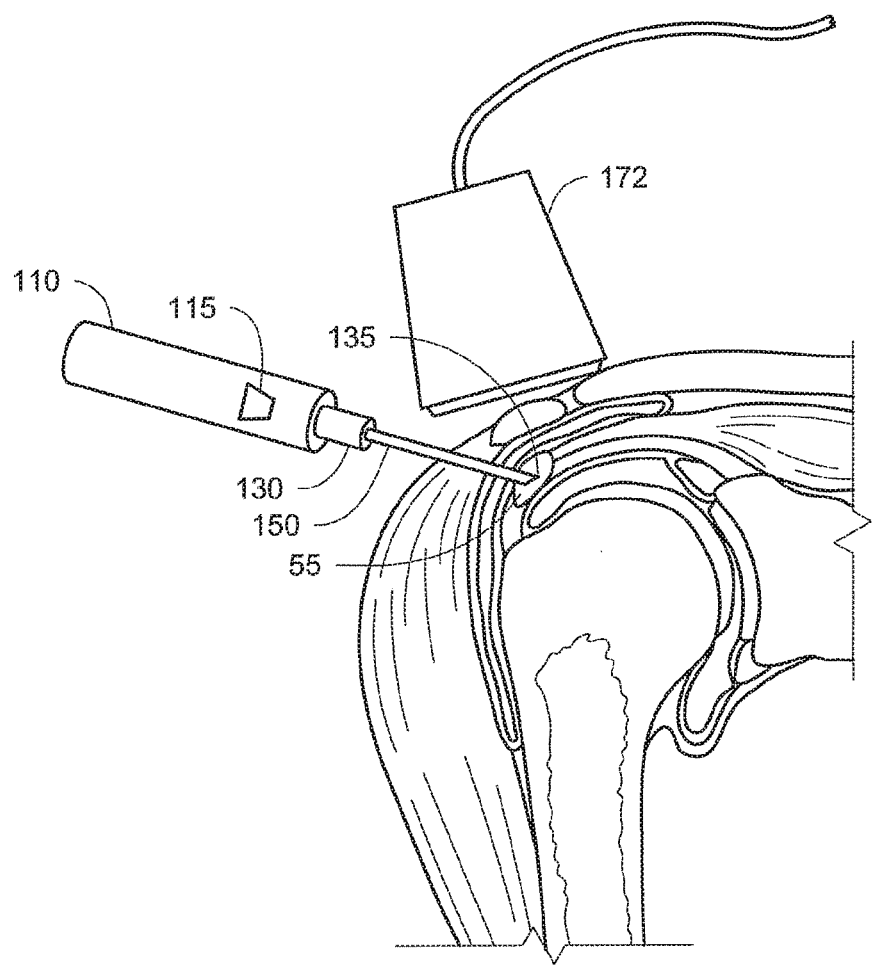
FIG. 2 is a cross-sectional view of body tissue that is accessed by the system in accordance with some embodiments.

FIG. 2 illustrates one example of the working instrument 130 may be used under the guidance of the ultrasound imaging equipment (using the ultrasound transducer 172) so as to treat targeted tendon tissue 55 om the rotator cuff of the shoulder joint. However, it should be understood from the description herein that the working instrument 130 may be used to act upon other tissue and may be used in other regions of the body. As previously described, the working instrument 130 may be used in a number of circumstances to provide soft tissue fenestration, disruption of osteocartilaginous lesions, and bony fenestration.

Referring again to FIG. 1, in another example, a working instrument 140 may include a working shaft 144 that fits within the cannula to provide irrigation and suction to the treated site. The working instrument 140 may include a connector 148 that releasably secures to the mating connector 118 of the driver device. Also, the working instrument 140 may include a connector 142 to releasably secure the proximal portion 152 of the cannula. As such, the cannula 150 can be releasably coupled to the driver device 110 while the working shall 144 resides therein.

The working shaft 144 may comprise a hollow tube having a distal opening 145 at the tip. The working shaft 144 may be smaller than the inner diameter of the cannula so that an outer lumen is defined therebetween. For example, when the working shaft 144 resides in the cannula 150, the working shaft may deliver an irrigation fluid (e.g., saline or the like) from a proximal port 141 and to the distal opening 145 while the outer lumen (between the cannula 150 and the working shaft 144) provides a suction action that removes the thud and debris out through the outlet port 143. In other embodiments, the fluid delivery and removal paths may be reversed.

In some circumstances, a pump mechanism may be connected to the coupler 146 and powered by the output shaft 116 of the motor 114 so as to provide the suction force. Alternatively, the input port 141 and the outlet port 143 may be connected to an independent suction device that delivers the irrigation fluid and that provides the suction force.

Figure 3:
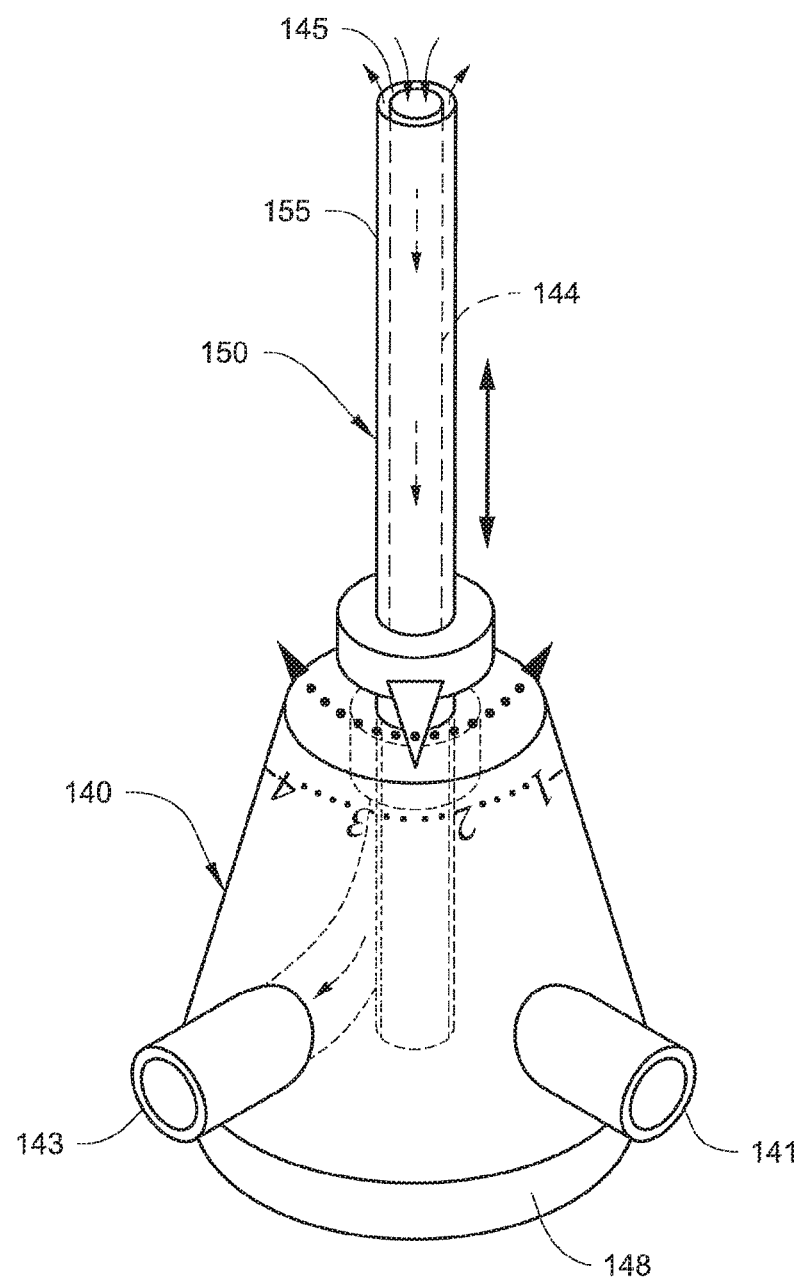
FIG. 3 is a perspective view of a portion of a system for accessing and treating tissue in accordance with some embodiments.

Other working instruments may be delivered to the cannula 150 so as to lavage affected areas. For example, FIG. 3 depicts an alternative construction for the suction instrument 140.

A number of other working instruments may be releasably secured to the driver device via the connector 118 or other locking mechanism. The working tips of these instruments can then be passed through the cannula 150 to the target area, traversing skin and unaffected tissues, thereby minimizing tissue trauma. It should be understood from the description herein that the working tips may be selected based upon the desired function at the targeted tissue 55. During a procedure, the driver device 110 may be powered off, the cannula 150 unlocked and left in place, and the working tip removed. The working instrument may be switched and then reattached to the cannula 150, or therapeutic or diagnostic substances may be delivered via the cannula 150 to the target site, or lavage and aspiration may be performed.

In another example, a working instrument may have a working shaft in the form of a pointed needle (constructed of, e.g., stainless steel, etc,). Such a working instrument may provide functionality similar to the working instrument 130 previously described in connection with FIG. 1. In some embodiments, the needle tips may include serrated tips for more aggressive disruption of scar, bony or cartilaginous protuberances, and soft tissue calcifications. This working instrument may also be used for periosteal stripping.

In another example, a working instrument may include a working instrument having a working tip its the form of a burr device. Such an instrument may include a stainless steel round or oval drill head. The working tip may be textured for tissue removal, and the working instrument or at least the working shaft may be disposable after a single use. The working shaft and working tip are configured to fit within the cannula 150. In some embodiments, the head width of the working tip may be about 16 gauge to about 27 gauge, and the extension length of the working shaft may be about 3 inches to about 0.25 inches. Such a working instrument can be used in a continuous rotational mode to drill or debride bone or cartilage lesions, or scarred or fibrotic tissue. Moreover, the working tip can be utilized to contour bony surfaces or create cavities in which therapeutic or diagnostic agents can be delivered.

In another example, a working instrument for use in the cannula 150 may include a shaver device in which the working shaft includes a hollow cylinder with a side port and inner serrated blade at the working tip. As previously described, the working tip may comprise a stainless steel material or other echogenic material that is viewable using the ultrasound imaging equipment 170. The working shaft and working tip are configured to fit within the cannula 150. In some embodiments, the head width of the working tip may be about 16 gauge to about 27 gauge, and the extension length of the working shaft may be about 3 Inches to about 0.25 inches. Such a working instrument can be used in a continuous rotational mode to drill or debride bone or cartilage lesions, or scarred or fibrotic tissue. In addition, the working shaft can be utilized to contour bony surfaces or create cavities in which therapeutic or diagnostic agents can be delivered.

Other working instruments may include working tips in the form of scalpel tips (e.g., to cut soft tissue structures, such as performing percutaneous release of ligament, tendon, plantar fascia, and similar structures) and blunt tips (e.g., a stainless steel, blunt tip used for probing). Furthermore, some working instruments may be used to delivery energy to the targeted tissue 55, such as working instrument that provides a radiofrequency treatment tip, a laser treatment tip, or a shock wave treatment tip.

Similar to the previously described suction instrument 140 (refer to FIG. 1) some working instruments may be configured to remove tissue and other debris from the targeted site. With many of the tissue removal instruments described herein, the use of the previously described expandable cannula may provide for the removal of larger debris.

Figure 4:
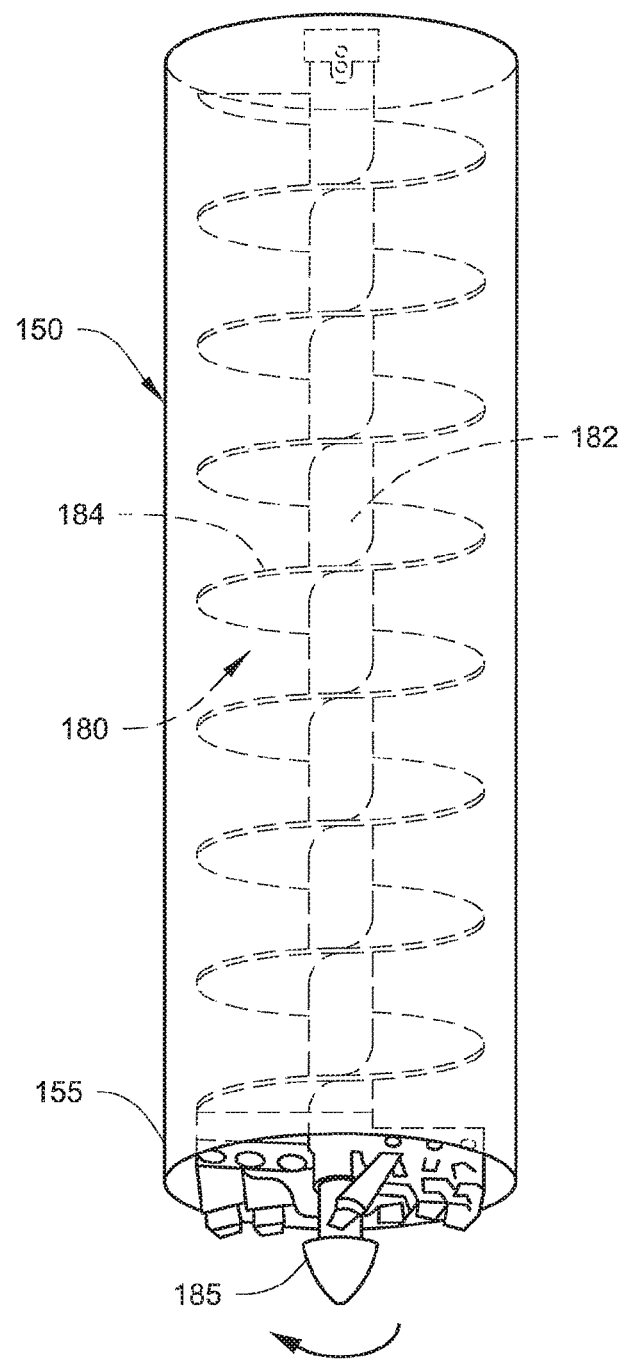
FIG. 4 is a perspective view of a portion of the system in accordance with another embodiment.

FIG. 4 shows one example of a working instrument 150 that serves to remove tissue through the portal of the access cannula 150. In this example, the working instrument 180 is in the form of a micro-augur device that includes a spiral pattern along its working shaft. The working instrument 180 is configured to be releasably connected to the driver device 110 so that the motor 114 (FIG. 1) provides the rotational motion to the micro-augur device. The working tip 185 of the instrument is configured to mechanically pull debris, fluid, and/or other material from the distal rip portion 155 of the cannula 150 to a reservoir outward of the patient's body. In some circumstances, reversing the rotational direction can push material from the base to the tip portion 155 of the cannula 150. In some embodiments, the shaft of the micro-augur device may be hollow to allow another shaft to rotate/reciprocate within it. This will allow simultaneous tissue destruction and aspiration of the debris generated. In another embodiment, the shaft 152 of the micro-augur instrument 180 may be hollow, with openings at its proximal and distal ends to permit fluid flow through the shaft 182, thereby allowing simultaneous irrigation and aspiration of the debris generated.

In another example of tissue removal, the cannula 150 may be used as a lavage conduit to the targeted tissue and surround areas. For instance, a syringe or surgical tubing may be hooked directly to the proximal end of the cannula 150, which then serves as a conduit for lavage, debridement, and aspiration. This may be facilitated by a one way external (e.g., outside the body) valve through which the operator may mechanically push fluid into the target area, after which time the inflow valve closes and outflow occurs to a bag or other collector. In some embodiments, this lavage process may be facilitated by gravity assist inflow or mechanical suction.

In another example of tissue removal, a working instrument in the form of a small-sized grasping device can be introduced into the cannula 150 to grab and remove debris and other material. In these circumstances, the grasping device may include two or more arms that can be actuated (e.g., by operation of the driver device 110 connected thereto) so as to move toward one another and grasp a piece of material. The grasping arms may comprise stainless steel or another echogenic material so that the arm movements can be monitored using the ultrasound imaging equipment 170.

Referring now to FIGS. 5-7B, some embodiments of the systems described herein may be in the form of a system 200 that includes a driver device 210 that is configured to actuate the working instrument 220 or 230 while generally avoiding cross-contamination. In such circumstances, the driver device 210 can be configured to be reusable, and the working instrument 220 or 230 can be disposable after one use. The working instruments 220 or 230 can be releasably connected to the driver device 210 in a manner that transfers power from the driver device 210 to the working tip 225 or 235 and in a manner so as not to contaminate the components of the driver device 210.

In the embodiment shown in FIG. 5, the driver device 210 is coupled to a working instrument 220 that provides rotational motion to the working shaft 224 and the working tip 225 (e.g., similar to the drill tip instrument 120 described in connection with FIG. 1). The driver device 210 includes a connector ring 218 that is bonded are attached to a sterile sheath 212 that covers all or a substantial portion of the entire driver device 210. As such, the user can grasp the housing 217 of the driver device 210 under the sheath 212 in a manner that provides substantially full tactile handling of the driver device 210 without contamination. The driver device 210 may include an electrically powered actuator (similar to previously described embodiments) that drives an output shaft 216 is a reciprocating axial motion (forward/rearward). A magnetic coupling is used to transfer the power of the driver device across the sterile field. For example, a magnetic device 215 can be joined to the output shaft 216 of the driver device 210 in proximity to an oppositely arranged magnetic device 225 of the working instrument 220. In this embodiment, the magnetic devices 215 and 225 are permanent magnets that having similar poles facing towards one another so as to repulse one another. As the output shaft 216 drives the longitudinal motion of first magnetic device 215 in the driver device 210, the second magnetic device 225 responds with a reactionary longitudinal suction. A spring device may be arranged to urge the second magnetic device 225 toward the first magnetic device 215 in those instances when the first magnetic device is pulled proximally away by the output shaft 216. In some embodiments, the driver device 210 may include an electromagnet connected to the actuator in place of the permanent magnet and motor. The electromagnet can provide the same reactionary longitudinal motion described above.

Figure 5:
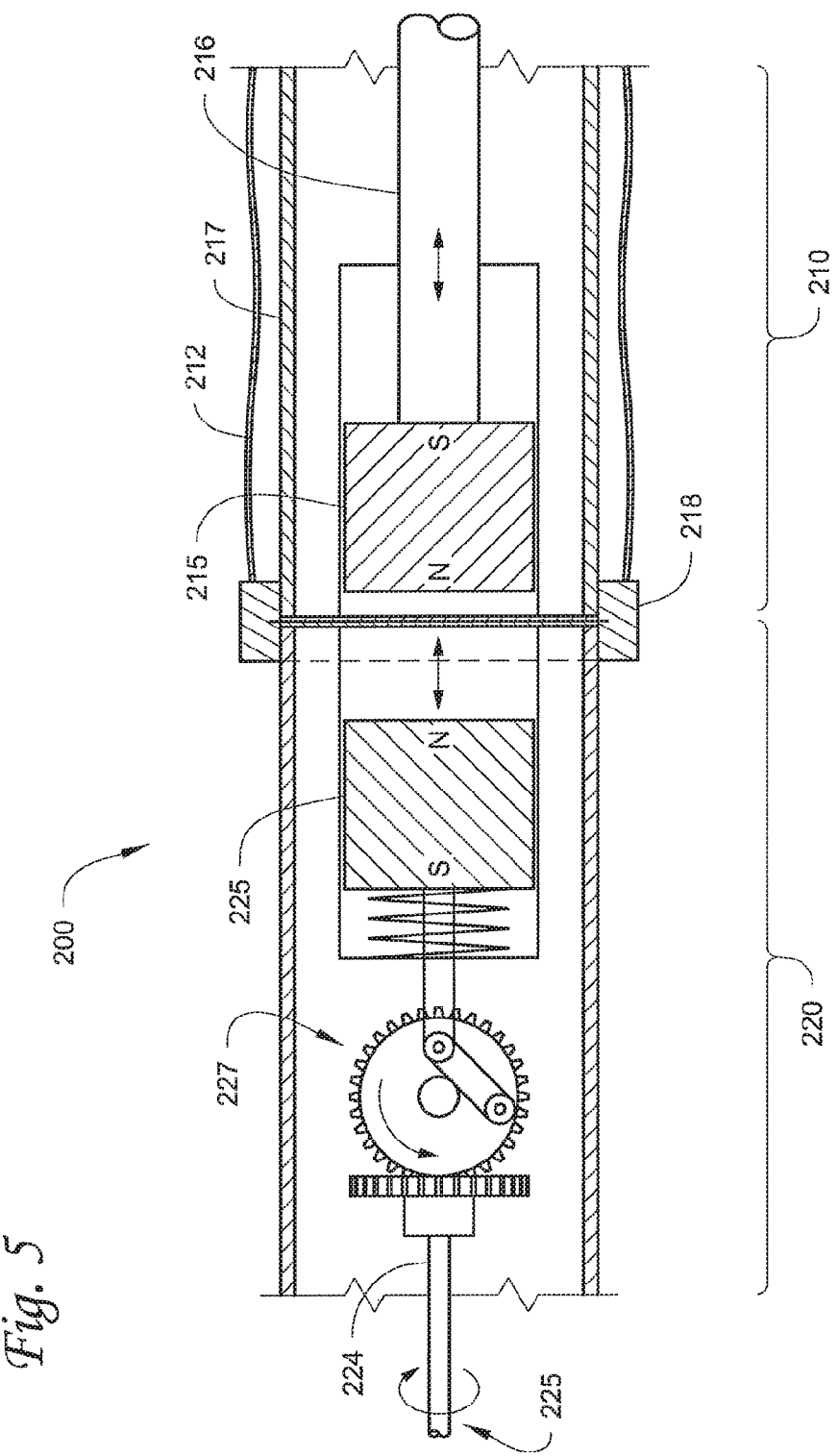
FIG. 5 is a cross-sectional view of a portion of a system for accessing and/or treating body tissue in accordance with some embodiments.

Still referring to FIG. 5, the working instrument 220 may include a gear mechanism 227 that transfers the reciprocating axial motion of the second magnetic device 225 into the rotational motion of the working shaft 224 and the working tip. Thus, the driver device 210 can control the motion of the working shaft 224 of the working instrument 220 without a direct physical connection to the output shaft 216 of the drive unit 210. Accordingly, the working instrument 220 can be introduced into, e.g., the access cannula 150 (FIG. 1) as previously described so as to act upon, e.g., the targeted tissue 53 (FIG. 1). Although the working instrument 220 may be exposed to tissue and bodily fluid during the procedure, the components of the driver device 210 may remain sterile due to the sheath 212 that protects the driver device 210. As such, the working instrument 220 may be disposed of after a single use (e.g., may be contaminated with tissue or bodily fluids) while the driver device 210 is generally uncontaminated and reusable.

Figure 6:
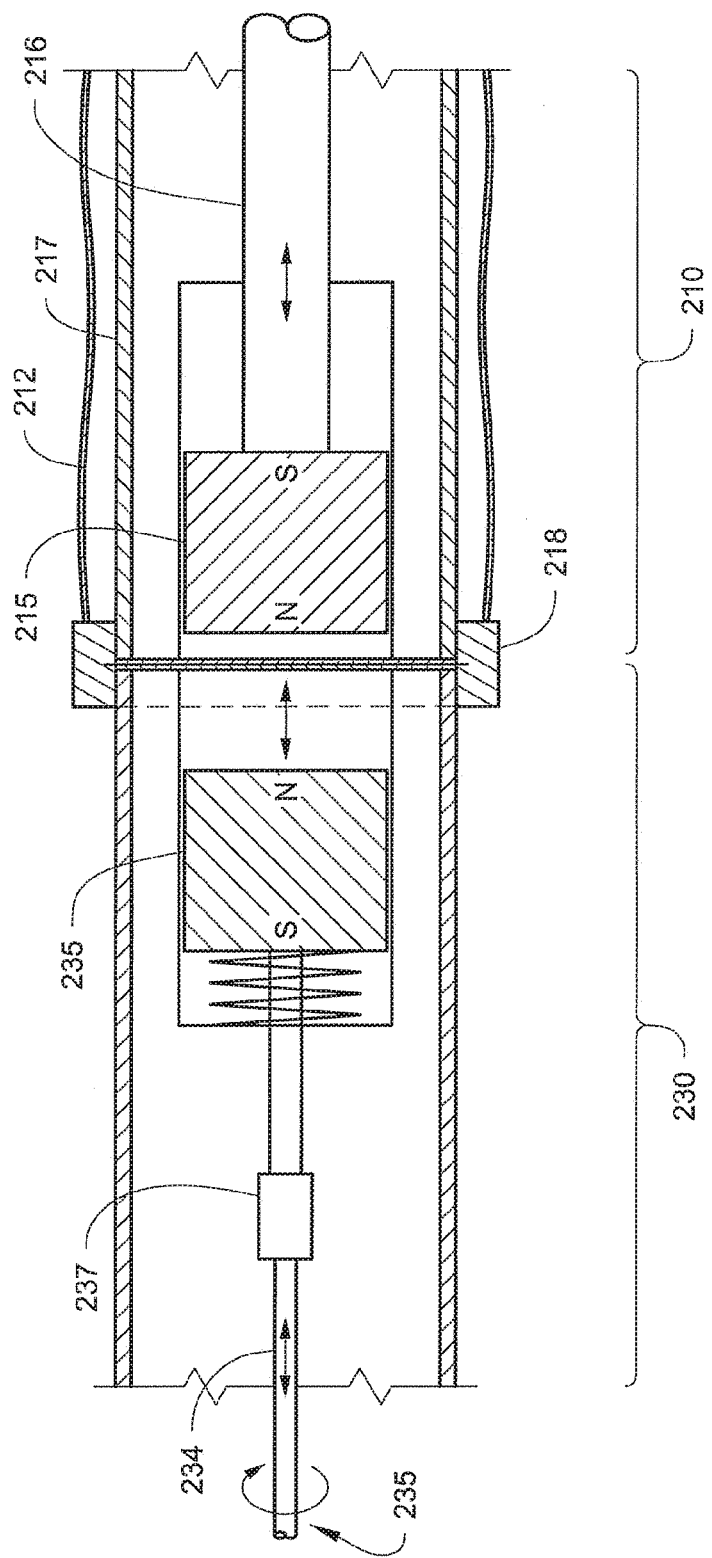
FIG. 6 is a cross-sectional view of a portion of the system of FIG. 5 in accordance with particular embodiments.

Referring to FIG. 6, the driver device 210 can be releasably secured to a working instrument 230 that provides reciprocating axial motion to the working shaft 234 and the working tip 235 (e.g., similar to the device 130 having the tapered tip as described in connection with FIG. 1). As before, the driver device 210 includes the connector ring 218 that is bonded are attached to the sterile sheath 212 that covers all or a substantial portion of the entire driver device 210. The output shaft 216 serves to reciprocating the first magnetic device 215 in the forward and rearward axial directions. In response to this motion, the opposing magnetic device 235 in the working instrument 230 also reciprocates in the axial direction. The opposing magnetic device 235 may be coupled to the working shaft 234 (e.g., via a coupler 237) so that the working shaft likewise reciprocates. Thus, the driver device 210 can control the motion of the working shaft 234 of the working instrument 230 without a direct physical connection to the output shaft 216 of the drive unit 210. The working instrument 230 can be introduced into, e.g., the access cannula 150 (FIG. 1) as previously described so as to act upon, e.g., the targeted tissue 53 (FIG. 1). As previously described, the working instrument 230 may be disposed of after a single use (e.g., may be contaminated with tissue or bodily fluids) while the driver device 210 is generally uncontaminated and reusable.

Referring to FIGS. 7A and 7B, in some embodiments, the protective sheath 212 may be integrally formed with or sandwiched between two halves of the connector ring 218. As such, the sheath 212 can provide a sterile barrier for the driver device 210 even when the working instrument 220 or 230 is connected thereto. In some circumstances, the sterile sheath 212 can be snugly fit along the outer surface of the housing 217 (FIG. 5) of the driver device 210. In other embodiments, the sheath 212 may serve as a loose covering over the device housing 217.

Accordingly, some embodiments of a medical systems described herein can be used to percutaneously access and act upon targeted tissue while reducing the likelihood of trauma to healthy soft tissue. The targeted tissue 53 can be accessed via the small-sized cannula 150 under the guidance of ultrasound imaging equipment 170. As described in more detail below, the systems may permit a patient to be treated in an office-based procedure under local anesthesia, thereby resulting in cost-savings to the patient by avoiding the costs of operating room time.

Referring now to procedures for treating the targeted site, the system 100 (or 200) may be used to access and treat body tissue as part of an office-based procedure under local anesthesia. Such procedures may include advancement and manipulation of components of the system 100 (or 200) under the guidance of the ultrasound imaging equipment 170. For example, some embodiments of the system 100 can be employed to perform: fenestration or release of scar tissue in tendon, ligament, muscle, and fascia; disruption and removal of soft tissue calcification; debridement of soft tissue, cartilage, or bone; soft tissue coagulation; burring and/or fenestration of bony surfaces; disruption and aspiration of cysts and fluid filled structures; delivery of therapeutic agents; tissue removal through coblation; tissue dilation; or a combination of two or more thereof.

In one example described hereafter, the system 100 (or 200) can be used to perform ultrasound-guided percutaneous tenotomy. In these circumstances, the patient may be supine on the table. The patient's arm can be at the side and resting on a pillow for support, and the elbow flexed at about 70-90 degrees. In some embodiments, diagnostic ultrasound examination is performed with a high-frequency linear transducer (e.g., a frequency greater than about 10 MHz) so as to identify and characterize the pathological tissue of the tendon in both longitudinal and transverse planes. After the pathological or other targeted tissue is identified, the lateral elbow may be prepared for insertion of the cannula 130 using an aseptic technique to reduce the risk of infection.

The targeted tissue and surrounding areas can be once again imaged in a longitudinal plane using, for example, a sterile ultrasound transducer cover and sterile ultrasound gel. Under direct guidance of the ultrasound imaging equipment, a local anesthetic (e.g., 5-10 cc of 1% lidocaine) can be delivered to the lateral elbow using a local needle injection (e.g., a 25 or 27 gauge needle using a layer by layer technique starting at the skin and penetrating down to the pathological tissue). In such circumstances, the anesthetic can be delivered to all areas expected to be treated, including the periosteum of the lateral epicondyle.

After the local anesthetic is delivered, the trocar device 160 and the cannula 150 are directed under the guidance of the ultrasound imaging equipment to the area of pathological tissue (refer, for example, to FIGS. 1-2). As previously described, the trocar 160 is disposed inside the cannula 150 and the combined instrument is passed to the pathological tissue under ultrasound guidance. After the cannula 150 is directed to the desired location (e.g., at or near the targeted pathological tissue, the trocar 160 is removed from the cannula 150, thereby leaving the cannula 150 as a portal through which a number instruments can be introduced to the site of pathology without necessarily traumatizing intervening tissue. As previously described, some of the instruments that can be introduced through the cannula 150 (e.g., utilized for the percutaneous tenotomy or for other treatments of body tissue) may include a working component that extends out of the distal opening 156 of the cannula 150. In addition, some of these instruments may comprise stainless steel or another echogenic material to provide a "visible" portion of the instrument when monitored using the ultrasound imaging equipment 170. Also, some of the instruments that can be introduced through the cannula 150 may releasably couple with the proximal portion 152 of the cannula 150 to provide a single construct for ease of maneuverability. For example, the user may manipulate the handle coupled to the working instrument so as to move both the cannula 150 and the instrument itself, thus maintaining a constant relationship between the mini-cannula and the working instrument.

In one example, the user may introduce the rasper device 130 (refer, for example, to FIG. 1) through the cannula 150 to break up calcifications and tough tendinopathic tissue. As previously described, the driver device 110 may be actuated to provide a forward-rearward longitudinal motion to the rasper device 130. Such a reciprocating motion of the tapered tip 135 can act upon the targeted tissue to break up calcifications and tough tendinopathic tissue in the targeted area. This treatment of the targeted tissue can be performed under ultrasound guidance (e.g., the pathological tissue can be visualized using the ultrasound imaging equipment) so that the user can verify that the pathological tissue has been addressed while minimizing or avoiding trauma to normal tissues. In some embodiments, if the lateral epicondyle exhibits significant enthesophytic changes, these can be abraded with the rasper device 130 as well. In some circumstances, the tapered tip 135 can also be utilized to puncture several holes into the lateral epicondyle to provide decortication that promotes the regrowth of healthy tissue. It should be understood from the description herein that, if the patient experiences discomfort at any point in the procedure, the working instrument can be removed and a stainless steel needle passed through the mini-cannula to deliver additional local anesthetic to the site. After the targeted tissue is disrupted and any bony pathology is addressed, the rasper device 130 can be released and removed from the cannula 150. During removal of the working instrument, the cannula 150 can remain in place with the distal tip portion residing proximate the targeted tissue.

In some circumstances, the operator can introduce the previously described suction-shaver device into the cannula 150 so as to debride the remaining targeted tissue. As previously described, the distal working tip of the suction-shaver device may provide a directional, motorized shaver. When the suction-shaver device is coupled with the cannula 150, the operator can control the direction of the suction-shaver device while suction is applied through the lumen of the suction-shaver device itself. As with the rasper device 130, the suction-shaver device can be decoupled and removed from the cannula 150. It should be understood from the description herein that, as an alternative to or in addition to the suction-shaver device 150, the operator may elect to lavage the area with a large bore, blunt tip stainless steel needle passed through the mini-cannula.

In this embodiment, after completion of rasping, enthesophyte removal, decortication, and debridement, the work upon the targeted tissue is generally completed with minimization of soft tissue trauma. Also in this embodiment no repair of the debridement site may be necessary due to naturally healing and regrowth of healthy tissue. If clinically indicated, the operator may instill therapeutic agents (e.g., autologus blood, platelet rich plasma, growth factors, hydrogel suspensions, or the like) into the operative site by passing a delivery device (e.g., a needle attached to a syringe or the like) through the cannula 150 residing in the patient's body.

It should be understood from the description herein that, in addition to or in the alternative to the working instruments described above, other working instruments in this system 100 may be introduced through the cannula 150 in certain circumstances. Such working instruments may include a drill tip instrument (e.g., device 130) that operates similar to the suction-shaver device, but has a small drill tip that protrudes longitudinally. This allows optimal visualization of the working drill tip end using the ultrasound imaging equipment. In some embodiments, the drill tip can be rounded to allow burring. The tip drill instrument can be used instead of the suction-shaver device to disrupt and debride pathological tissue. In addition, it may be useful to burr down enthesophytes and facilitate decortication of the lateral epicondyle when clinically indicated. In another example, the suction device 140 (FIG. 1) may be an instrument that is introduced into the cannula 150. Other examples include: a grabber device (e.g., a stainless-steel or equivalent instrument used to grab and remove calcific deposits and debris) that includes as alligator-like mouth which opens and closes; a spreader device (e.g., a stainless-steel or equivalent instrument that can be actuated to spread two distal arms away from each other) that may be used to bluntly open up a working space or bluntly dissect through tissue; a cautery device that activate to cauterize tissue and control bleeding; a radiofrequeney probe sized to fit through the cannula 150; a radiofrequency coblation probe sized to fit through the cannula 150; an ultrasonic agitator sized to fit through the cannula 150; a shock-wave device sized to fit through the cannula 150; or a combination thereof.

After the targeted tissue is treated and the cannula 150 is removed from the patient's skin, the patient can be discharged to home after a short period of in office observation. In these circumstances, post-procedure pain is variable, ranging from essentially no pain to moderately severe pain, and may last less than 72 hours. Thus, the system 100 provides for an office-based procedure under local anesthesia, thereby resulting in cost-savings to the patient by avoiding the costs of operating room time. In some embodiments, a patient may only need ice or cooling packs for analgesia and edema control after the treatment (and may be encouraged to avoid anti-inflammatories). Optionally, the patient may receive narcotic analgesics to use short-term as needed.

The words "preferred" and "preferably" as used herein refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, a coblation probe may refer to one, two or more coblation probes.

The term "and/or" means one or all of the listed elements or a combination of any two or more of the listed elements.

The complete disclosure of the patents, patent documents, and publications identified herein are incorporated by reference in their entirety as if each were individually incorporated.

Illustrative embodiments are discussed and reference has been made to possible variations within the scope of this disclosure. These and other variations and modifications will be apparent to those skilled in the art without departing from the scope of the invention, and it should be understood that this invention is not limited to the illustrative embodiments set forth herein. Accordingly, the invention is to be limited only by the claims provided below and equivalents thereof.

The invention claimed is:

1. A system for treating body tissue under guidance of ultrasound instrumentation, the system comprising:
    a cannula configured to percutaneously access targeted tissue, the cannula comprising a distal tip portion that comprises echogenic material so as to be viewable by ultrasound imaging equipment;
    an elongate working instrument that is insertable into a proximal opening of the cannula and through a distal opening of the cannula, the elongate working instrument comprising a working shaft that comprises a working tip configured to act upon the targeted tissue, the working tip comprising echogenic material so as to be viewable by ultrasound imaging equipment;
    a handheld driver unit having a powered actuator to drive the working tip of the elongate working instrument to act upon the targeted tissue, wherein the handheld driver unit is releasably securable to the cannula such that at least a portion of the elongate working instrument resides in the cannula; and
    a magnetic coupling positioned between the powered actuator and the working instrument, the magnetic coupling configured to transfer power from the powered actuator to the elongate working instrument across a sterile field, wherein the magnetic coupling comprises at least a first magnet positioned on a first side of the sterile field and at least a second magnet positioned on a second side of the sterile field that is opposite to the first side, the at least two magnetic elements positioned along a single axis and each configured to move along the single axis.

2. A system according to claim 1, wherein the cannula comprises an adjustable length such that the distance between the distal tip portion of the cannula and the handheld driver unit is adjustable.

3. A system according to claim 1, wherein the cannula comprises an adjustable cross-sectional area.

4. A system according to claim 1, wherein the cannula comprises a lateral width of about 12 gauge or less.

5. A system according to claim 1, further comprising a trocar located within the cannula, wherein the trocar comprises a pointed tip protruding from the distal tip portion of the cannula.

6. A system according to claim 1, wherein the working tip of the working instrument is selected from the group consisting of a drill tip, a chisel tip, a burr device, and a micro-augur device.

7. A system according to claim 1, wherein the working shaft comprises an adjustable length, wherein the distance between the working tip and the proximal opening of the cannula is adjustable.

8. A system according to claim 1, wherein the working shaft is smaller than an inner diameter of the cannula such that an outer lumen is defined between the working shaft and the inner diameter of the cannula.

9. A system according to claim 1, wherein the working shaft comprises a hollow working shaft such that fluid can pass between a proximal port and a distal opening of the working shaft.

10. A system according to claim 9, wherein the working tip comprises a micro-auger.

11. A system according to claim 1, wherein the working shaft is smaller than an inner diameter of the cannula such that an outer lumen is defined between the working shaft and the inner diameter of the cannula, and the working shaft comprises a hollow working shaft such that fluid can pass between a proximal port and a distal opening of the working shaft.

12. A method of ultrasound-guided percutaneous tenotomy using the system of claim 1, the method comprising:
    disposing an ultrasound transducer device of ultrasound imaging equipment over a portion of skin proximate to targeted tendon tissue;
    monitoring under the guidance of the ultrasound imaging equipment the insertion of the echogenic distal tip portion of the cannula toward the targeted tendon tissue;
    releasably securing the handheld driver unit to a proximal portion of the cannula extending outside the skin such that the elongate working instrument coupled to the handheld driver unit resides at least partially in the cannula; and
    viewing a display of the ultrasound imaging equipment as the working tip of the working shaft of the elongate working instrument acts upon the targeted tendon tissue.

13. A method according to claim 12, wherein the cannula comprises an adjustable length, and wherein the method comprises adjusting the distance between the distal tip portion of the cannula and the handheld driver unit.

14. A method according to claim 12, wherein the working shaft comprises an adjustable length, and wherein the method comprises adjusting the distance between the working tip and the proximal opening of the cannula.

15. A method according to claim 12, wherein the working shaft is smaller than an inner diameter of the cannula such that an outer lumen is defined between the working shaft and the inner diameter of the cannula, and wherein the method comprises moving fluid through the outer lumen.

16. A method according to claim 12, wherein the working shaft comprises a hollow working shaft such that fluid can pass between a proximal port and a distal opening of the working shaft, and wherein the method comprises moving fluid through the hollow working shaft.

17. A method according to claim 12, wherein the working shaft is smaller than an inner diameter of the cannula such that an outer lumen is defined between the working shaft and the inner diameter of the cannula, and the working shaft comprises a hollow working shaft such that fluid can pass between a proximal port and a distal opening of the working shaft, wherein the method comprises moving fluid through the outer lumen and the hollow working shaft.

18. A method according to claim 12, wherein the ultrasound transducer device comprises a high-frequency linear transducer that operates at a frequency greater than about 10 MHz.

\* \* \* \* \*